(12) United States Patent
Vafi et al.

(10) Patent No.: US 6,488,409 B1
(45) Date of Patent: Dec. 3, 2002

(54) X-RAY DETECTOR IMAGE QUALITY TEST TECHNIQUES

(75) Inventors: Habib Vafi, Brookfield, WI (US); Farshid Farrokhnia, Brookfield, WI (US); Donald F. Langler, Brookfield, WI (US); Kenneth S. Kump, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/681,785

(22) Filed: Jun. 5, 2001

(51) Int. Cl.[7] ............................................... G01D 18/00

(52) U.S. Cl. ....................................... 378/207; 378/98.8

(58) Field of Search ............................ 378/207, 19, 98, 378/98.8

(56) References Cited

U.S. PATENT DOCUMENTS 6,418,241 B1 * 7/2002 Schreiner ............... 250/370.09

* cited by examiner

*Primary Examiner*—Robert H. Kim
*Assistant Examiner*—Courtney Thomas
(74) *Attorney, Agent, or Firm*—McAndrews, Held & Malloy, Ltd.; Peter J. Vogel; Michael A. Dellapenna

(57) ABSTRACT

An x-ray system (10) include a digital detector (400) that defines two regions: a first region (404) suitable for generating data useful for creating a patient x-ray image and a second region (406) less suitable for generating such data than the first region. A source (20) transmits x-rays through a phantom (420) located between the source and the second region (406) so that the detector (400) generates test data in the second region. A processor (302) measures at least one parameter in response to the test data and stores a value of the parameter at one point of time. The processor compares the first value with a second value of the one parameter generated at a later second point in time. The processor also generates a result signal representing the results of the comparison.

18 Claims, 5 Drawing Sheets

MTF @ 1.0 lp/mm= 88.55%
MTF @ 2.0 lp/mm= 73.86%
MTF @ 5.0 lp/mm= 29.02%
MTF Area= 6.78
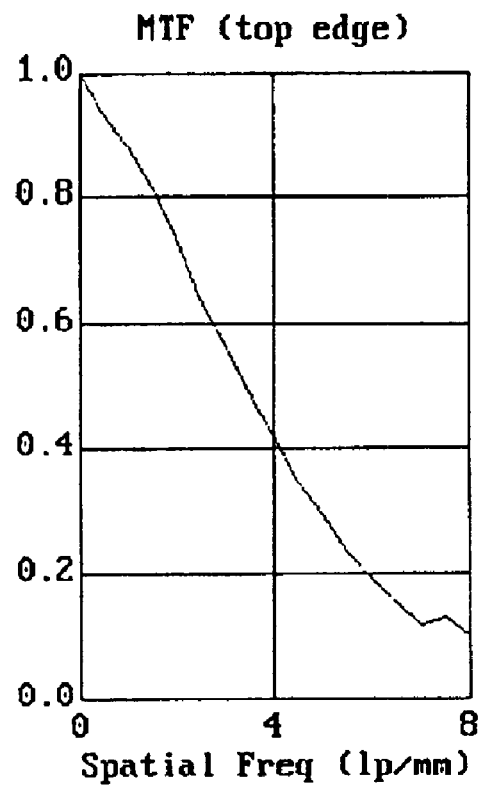
Fig. 5

X-RAY DETECTOR IMAGE QUALITY TEST TECHNIQUES

BACKGROUND OF INVENTION

This invention relates to x-ray detectors and more specifically relates to techniques for testing such detectors.

Almost all image quality evaluation methods rely on placing off-the-shelf or custom-made x-ray phantoms in the field of view. Some methods use image processing and analysis tools to automatically detect regions of interest in the acquired image of the phantom. These methods have a significant advantage over "manual" methods that rely heavily on human operators to perform these measurements. These methods also provide more consistent and objective measurements.

However, automating the analysis of the image of the phantom does not result in full automation of the image quality evaluation, because, like the "manual" methods, they still require intervention by a human operator to place the x-ray phantom(s) in the field of view. Experience has shown that human operators are not inclined to take the time to place the x-ray phantom in the field of view. As a result, detector problems may go undetected for some time. X-ray images generated while the detector problems go undetected can result in degraded image quality.

This invention addresses these problems and provides a solution.

SUMMARY OF INVENTION

The preferred embodiment is useful in an x-ray system comprising a digital detector defining a first region suitable for generating data useful for creating a patient x-ray image and a second region less suitable for generating such data than the first region. In such an environment, the detector can be tested by providing a source of x-rays and a phantom located between the source and at least a portion of the second region so that the detector generates detector test data in at least a portion of the second region in response to the x-rays. At least one parameter is measured in response to at least a portion the test data. A first value of the one parameter is stored at one point of time. A comparison is made of the first value with a second value of the one parameter generated at a second point in time later than the first point of time. A result signal representing the results of the comparison is generated.

By using the foregoing techniques, the detector can be tested without human intervention, thereby insuring more reliable and timely testing than has been possible in the past.

BRIEF DESCRIPTION OF DRAWINGS

FIG. 5 is graph illustrating an exemplary plot of modulation transfer function versus spatial frequency of phantom grids.

DETAILED DESCRIPTION

Figure 1:
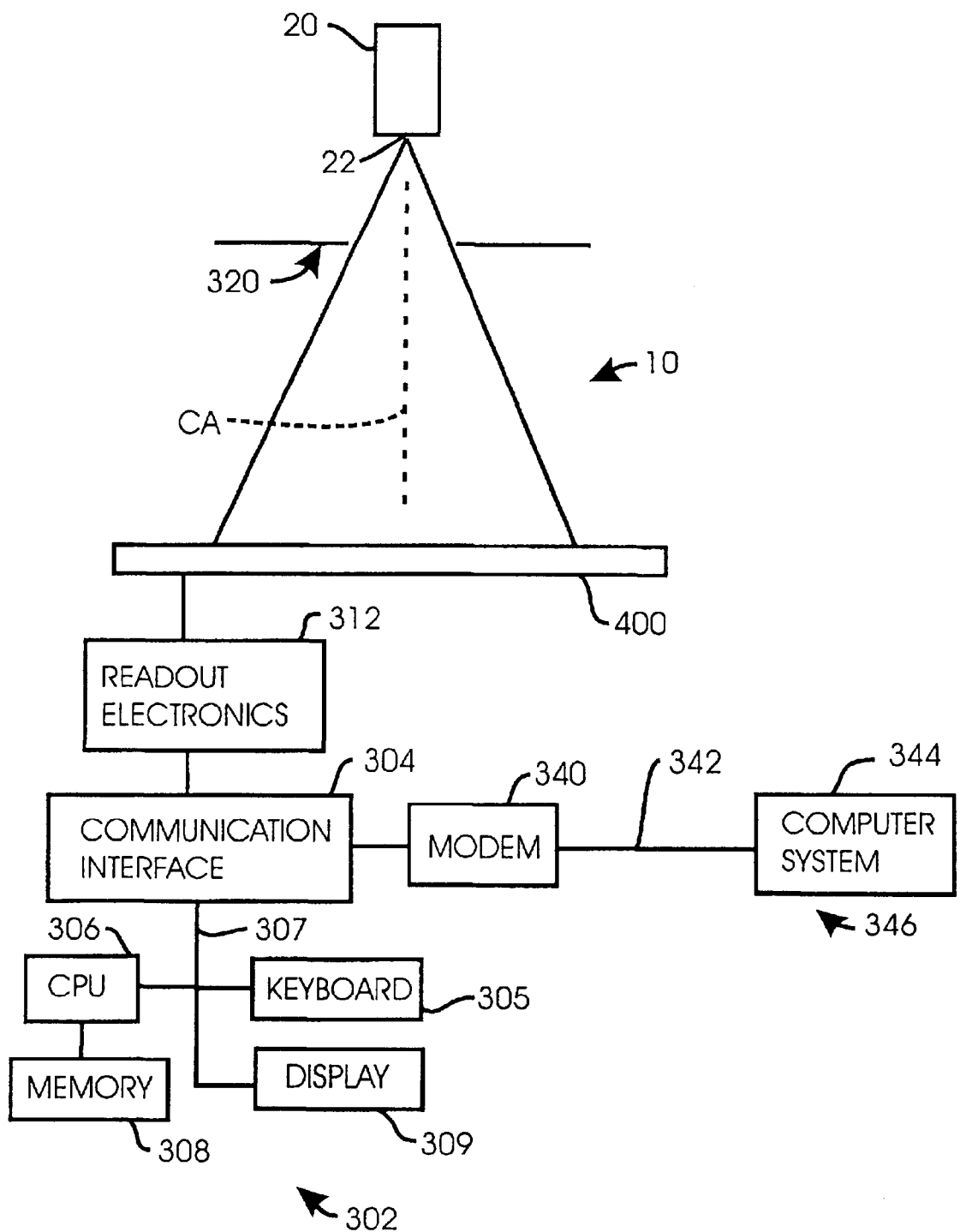
FIG. 1 is a schematic block diagram of an exemplary form of x-ray system employing a preferred embodiment of the invention.

Referring to FIG. 1, a preferred form of x-ray imaging system 10 made in accordance with the invention comprises an x-ray tube 20 that generates x-rays from a focal spot 22 and directs the x-rays in relationship to a central axis CA. A digital image detector 400 detects the x-rays in a well-known manner. A collimator 320 includes collimator blades shown schematically in FIG. 1.

A calibration processor 302 includes communication interface or module 304, a keyboard 305, a central processing unit (CPU) 306, a memory 308 and a display unit 309, such as a computer monitor, all coupled by a bus 307 as shown. The processor may include, for example, a microprocessor, digital signal processor, microcontroller or various other devices designed to carry out logical and arithmetic operations. Signals corresponding to an x-ray image are read from detector 400 by readout electronics 312. The design and operation of most of the components with numbers greater than 300 are described in more detail in application Ser. No. 09/342,686, filed Jun. 29, 1999, in the names of Kenneth S. Kump et al., entitled "Apparatus And Method For x-ray Collimator Sizing And Alignment," assigned to General Electric Company and incorporated by reference in its entirety into this specification.

Communication interface 304 is coupled through a modem 340 and a network 342, such as the Internet, to a computer system 344 at a remote location 346. Maintenance personnel at location 346 monitor computer system 344 to determine if detector 400 requires repair or maintenance.

Figure 2:
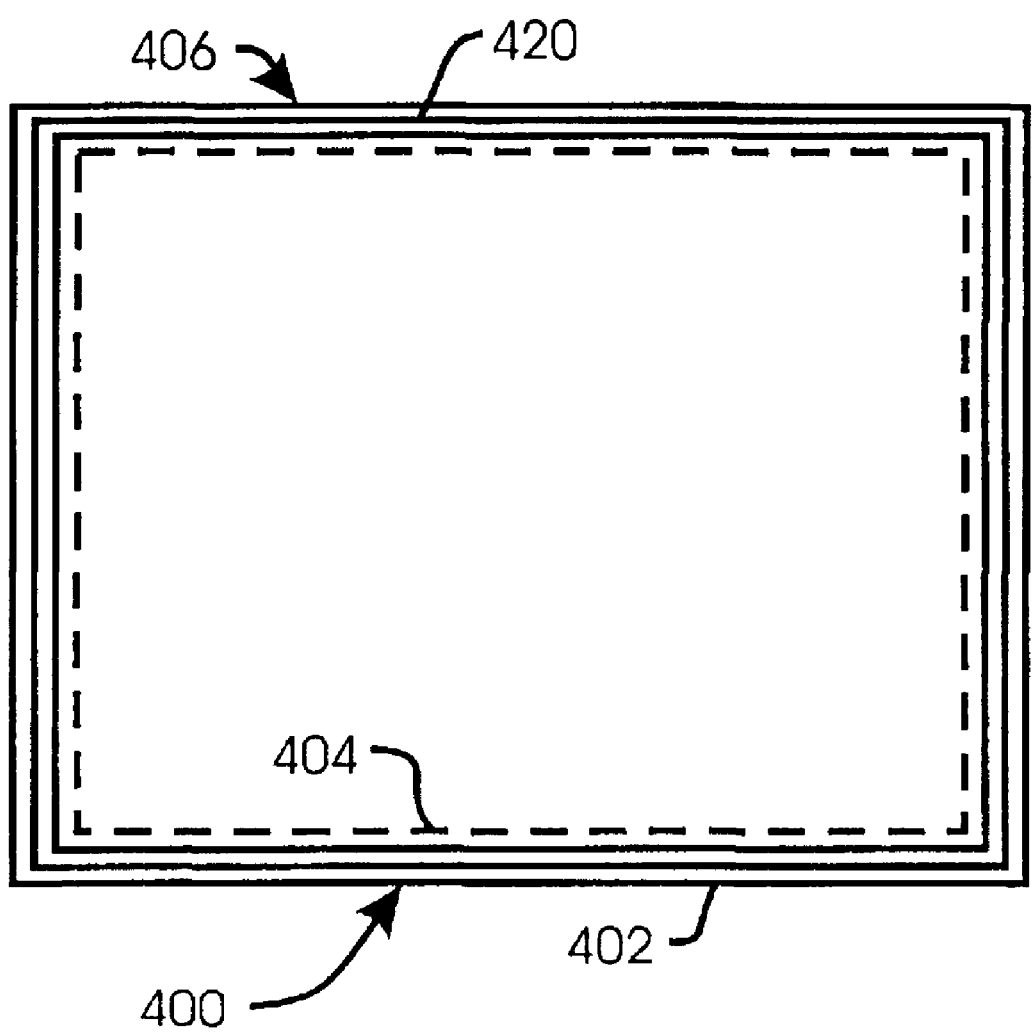
FIG. 2 is a schematic top plan view of the detector shown in FIG. 1 illustrating different regions of the detector and also schematically illustrating a preferred form of phantom made in accordance with the invention.

FIG. 2 is a top plan view of detector 400 that defines an outer periphery 402 and an inner region 404 that is suitable for generating data useful for creating a patient x-ray image. Between region 404 and periphery 402 is a margin region 406 less suitable for generating data useful for creating a patient x-ray image than region 404. Region 406 is typically about 2–3 millimeters (mm) wide. Within region 406 is a generally rectangular saw tooth strip phantom 420.

Figure 3:
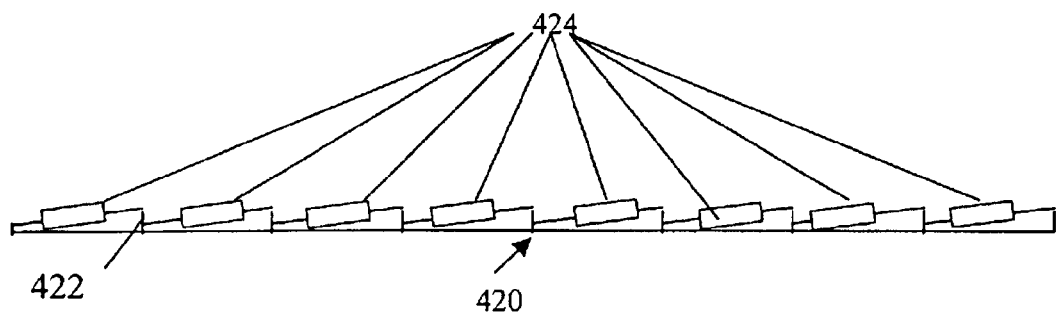
FIG. 3 is a schematic, fragmentary, side elevational view of the phantom shown in FIG. 2.

A fragment of phantom 420 is shown in FIG. 3. Phantom 420 comprises a frame 422 substantially transparent to x-rays and identical regions of interest (ROIs) or coupons 424 that absorb x-rays. The ROIs are separated by identical distances of about 10 mm and have dimensions of about 10 by 2 mm.

Figure 4:
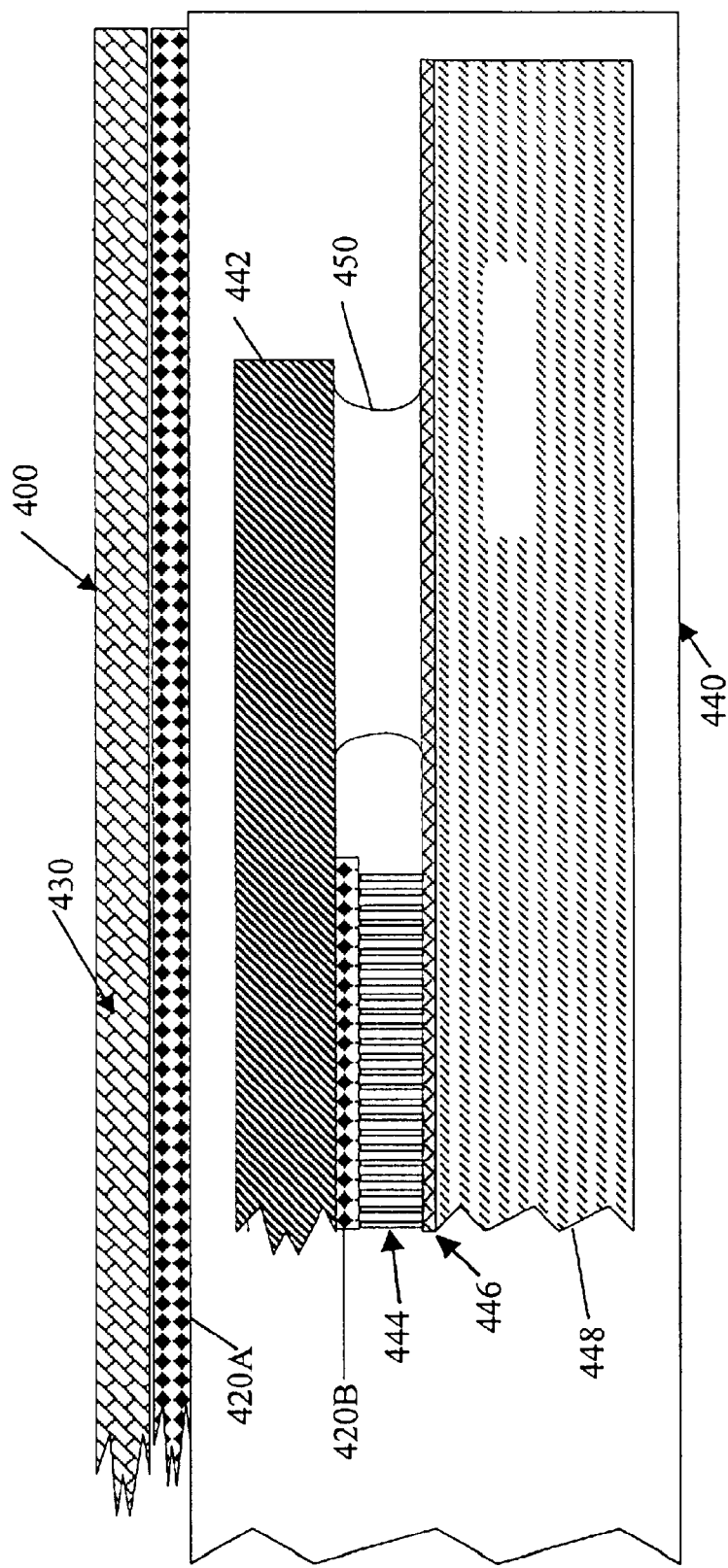
FIG. 4 is an enlarged fragmentary top plan view of the phantom shown in FIG. 3 together with adjacent portions of the detector shown in FIGS. 1 and 2.

Referring to FIG. 4, phantom 420 may be located in one of at least two different positions. For example, phantom 420A is located directly under cover 430 of detector 400. The location of phantom 420A has the advantage of being accessible for replacement and service. However, phantom 420B may be positioned more accurately than phantom 420A by being located inside a sealed metal box or cabinet 440. As shown in FIG. 4, phantom 420B is located below an aluminum graphite cover 442 and above a scintillator 444. An amorphous silicon array 446 is located below scintillator 444 and is carried by a glass substrate 448. A seal 450 is provided between cover 442 and array 446 to protect scintillator 444.

FIG. 5 illustrates an x-ray image of a tungsten coupon sub-phantom and a modulation transfer function (MTF) curve computed based on the upper edge profile of the tungsten coupon. FIG. 5 also shows how the edge profile of a rectangular tungsten coupon can be used to compute MTF. The coupon illustrated in FIG. 5 is about 30 mm by 30 mm. The vertical axis in FIG. 5 indicates modulation strength and the horizontal axis indicates spatial frequency of the tungsten coupons. The profiles of vertical and horizontal edges of the coupon can be used to compute MTF in horizontal and vertical directions, respectively. The coupon is deliberately positioned at a slightly rotated angle with respect to the top surface of detector 400 to avoid the edge points from lining up along a row or column.

In general, phantom 420 is used to conduct a self-test of certain image quality (IQ) parameters of solid state digital x-ray detector 400. Phantom 420 is located in margin region 406 of detector 400. Image data from pixels in margin 406 of the detector is created when x-rays are transmitted through phantom 420 to detector 400. A certain number of rows and columns of data in the margin 406 are read out but are not displayed. This is because the process used to make the detector panels does not always result in uniform deposition of the cesium iodide (x-ray scintillator) on the edges (e.g., region 406), compared to the rest of the panel (e.g., region 404).

By planting small x-ray phantoms, such as phantom 420, in these unused margins (e.g., margin 406), it is possible to compute certain image quality parameters. For example, a narrow "edge" phantom as shown in FIGS. 3 and 4 can be used to compute the modulation transfer function (MTF), at every exposure as illustrated in FIG. 5. Alternatively, the noise power spectrum or contrast to noise ratio, can be calculated in this margin region.

Specifically, for MTF, an edge-based method of computation can be utilized, based on edge profiles along the diagonal side of each saw tooth of the type shown in FIG. 3.

Usually, measuring IQ parameters of a x-ray detector involves placing a known x-ray phantom in the field of view, acquiring an image and then processing it to compute the IQ parameters. The use of implanted sub-phantoms, such as phantom 420, inside the detector 400 eliminates the need for an external phantom, and more importantly the need for an operator to place the phantom.

In addition to providing the necessary sub-phantoms, such as phantom 420, and an image, a "qualifying" algorithm is used. This algorithm is executed by CPU 306 and ensures that the image data being received in margin 406 are of good enough quality. That is, the x-ray field must be uniform (or be correctable) and the detector quality must be adequate. This is important since patients will be imaged simultaneously while the self-test of the detector is being conducted. This is a feature which limits the amount of x-ray radiation received by the patient. Technologists using good practice will collimate to the interesting patient anatomy. We are relying on the scattered radiation and occasionally "raw" (un-attenuated) radiation to expose phantom 420 in margin region 406. The qualifying algorithm computes simple statistics in the region of phantom 420 or the parts of region 406. For example, the mean, minimum, maximum, and standard deviation of gray levels (counts) can be determined. These values are compared to predefined limits to determine if the image data is valid for subsequent calculation. Additional details about the qualifying algorithm are as follows:
Step1) There is first a need to define which ROIs are acceptable for computation. An initial "Pre-calibraion" to select ROIs with acceptably low number of bad pixels, minimum conversion factor (CF), and define a response correlation to the known good area in the region of the detector suitable for creating a patient x-ray image is required. This is conducted once per detector calibration which may occur, for example, roughly yearly.

Step 2) Of the ROIs deemed acceptable in step 1, for each exposure, there are additional acceptance criteria such as: minimum contrast between x-ray absorbing and x-ray transparent areas, and minimum signal count. Only the ROIs passing both step 1 and step 2 criteria will be used in the calculation.

After the image data is qualified, CPU 306 executes another algorithm to analyze the data and produce summary data, such as MTF data. Additional details about the MTF algorithm are as follows:Calculate MTF by a) Starting with the $12^{th}$ row or column in from the edge of the panel, for an ROI, record the signal response vs the location of the edge; b) Increment until all rows or columns crossing the edge of the imbedded phantom have been sampled; c) Fourier transform the data set; d) Extract the frequency coefficients; e) Normalize the data for each frequency and adjust per the correlation defined in step 1; f) Repeat steps a–e for each acceptable ROI; and g) average all the ROI results.

This summary data is then placed into log files in memory 308 that can be actively "swept" using remote diagnostic equipment embodying computer system 344. Alternatively, the process may proactively call-out to a remote host 344 (at on-line-center) to report its data. This may be done on a scheduled timeline, or when particular events occur (e.g.: values fall below certain pre-defined levels indicating failure or imminent failure). However, as a self-test, what is important is detection of any variations in the MTF on the edges, not the absolute MTF. The creation of summary reports includes the appending of new qualifying data to the "log" files. The data includes a parameter, such as MTF. A process may be included which compares the new data or parameter (or results from trending of current plus previous data) to predefined or calculated parameter thresholds that were previously stored. CPU 306 generates a result signal indicating the results of the comparison. When these thresholds are exceeded, a result signal or a message is sent to remote computer system 344 via modem 340 and the Internet to indicate a problem or status. For example, a message indicating a problem may be sent if the MTF summary data describing an MTF curve like the one shown in FIG. 5 from a previous year is more than 10 percent different from current summary data describing a current MTF curve. All of the foregoing data and parameters may be displayed on display 309.

Using implanted sub-phantoms, such as phantom 420, in the unused margins of the detector (e.g., region 406) allows testing and evaluation of certain parameters of the detector during a normal patient image acquisition. This self-test capability can be used to collect IQ data during every "scan". Analyzing the data over time can be used to identify possible change or degradation of IQ of the detector in a pro-active fashion. This design results in further automation of image quality evaluation of solid state x-ray detectors. It eliminates or minimizes the reliance on human operators to perform the IQ evaluation on a regular basis, making it possible to be truly pro-active in servicing it.

Those skilled in the art will recognize that the preferred embodiments may be alteredand modified without departing from the true spirit and scope of the invention as defined in the accompanying claims.

What is claimed is:

1. In an x-ray system comprising a digital detector defining a first region suitable for generating data useful for creating a patient x-ray image and a second region less suitable for generating such data than said first region, apparatus for testing the detector comprising:

a source of x-rays;

a phantom located between said source and at least a portion of the second region so that said detector generates detector test data in at least a portion of the second region in response to said x-rays; and a processor arranged to measure at least one parameter responsive to at least a portion said test data, store a first value of said one parameter at one point of time, make a comparison of said first value with a second value of said one parameter generated at a second point in time later than said first point of time; and generate a result signal representing the results of said comparison.

2. Apparatus, as claimed in claim 1, wherein said first and second parameters comprise modulation transfer functions.

3. Apparatus, as claimed in claim 1, wherein said processor is arranged to generate said result signal when said first and second values fall within a predetermined tolerance.

4. Apparatus, as claimed in claim 1, and further comprising a communication module arranged to transmit said result signal to a remote location.

5. Apparatus, as claimed in claim 1, wherein said detector comprises a solid-state detector.

6. Apparatus, as claimed in claim 1, and further comprising a display arranged to display at least said first value.

7. Apparatus, as claimed in claim 1, wherein said processor is arranged to generate qualified test data in response to said detector test data and to measure said at least one parameter responsive to said qualified test data.

8. Apparatus, as claimed in claim 7, wherein said processor is arranged to generate said qualified test data by generating statistical values in response to said qualified data based on one or more of mean values, minimum values, maximum values and standard deviation values, and comparing the statistical values with one or more limits.

9. Apparatus, as claimed in claim 1, wherein the second region comprises a margin region.

10. In an x-ray system comprising a digital detector defining a first region suitable for generating data useful for creating a patient x-ray image and a second region less suitable for generating such data than said first region, a source of x-rays, a phantom located between said source and at least a portion of the second region so that said detector generates detector test data in at least a portion of the second region in response to said x-rays, and a processor, a method for testing the detector comprising:

measuring at least one parameter responsive to at least a portion of said test data;

storing a first value of said one parameter at one point of time;

comparing said first value with a second value of said one parameter generated at a second point in time later than said first point of time; and generating a result signal representing the results of said comparison.

11. A method, as claimed in claim 10, wherein said first and second parameters comprise modulation transfer functions.

12. A method, as claimed in claim 10, wherein said generating comprises generating said result signal when said first and second values fall within a predetermined tolerance.

13. A method, as claimed in claim 10, and further comprising transmitting said result signal to a remote location.

14. A method, as claimed in claim 10, wherein said detector comprises a solid-state detector.

15. A method, as claimed in claim 10, and further comprising displaying at least said first value.

16. A method, as claimed in claim 10, and further comprising:

generating qualified test data in response to said detector test data; and measuring said at least one parameter responsive to said qualified test data.

17. A method, as claimed in claim 16, wherein said generating said qualified test data comprises:

generating statistical values in response to said qualified data based on one or more of mean values, minimum values, maximum values and standard deviation values, and comparing the statistical values with one or more limits.

18. A method, as claimed in claim 10, wherein the second region comprises a margin region.

* * * * *